United States Patent
Shah et al.

(10) Patent No.: US 10,463,674 B2
(45) Date of Patent: *Nov. 5, 2019

(54) PROCESS FOR MANUFACTURING STERILE OPHTHALMIC PHARMACEUTICAL SUSPENSIONS

(71) Applicant: Sentiss Pharma Private Limited, New Delhi (IN)

(72) Inventors: Mandar V. Shah, New Delhi (IN); Deepak Bahri, New Delhi (IN); Divya Pandit, New Delhi (IN)

(73) Assignee: Sentiss Pharma Private Limited, New Delhi (IN)

( * ) Notice: Subject to any disclaimer, the term of this patent is extended or adjusted under 35 U.S.C. 154(b) by 0 days.

This patent is subject to a terminal disclaimer.

(21) Appl. No.: 15/034,306

(22) PCT Filed: Nov. 5, 2014

(86) PCT No.: PCT/IB2014/065806
§ 371 (c)(1),
(2) Date: May 4, 2016

(87) PCT Pub. No.: WO2015/068105
PCT Pub. Date: May 14, 2015

(65) Prior Publication Data
US 2016/0279139 A1    Sep. 29, 2016

(30) Foreign Application Priority Data

Nov. 8, 2013   (IN) .......................... 3298/DEL/2013

(51) Int. Cl.
| | | |
|---|---|---|
| A61K 31/542 | (2006.01) | |
| A61K 9/00 | (2006.01) | |
| A61K 9/08 | (2006.01) | |
| A61K 47/02 | (2006.01) | |
| A61K 47/18 | (2017.01) | |
| A61K 47/26 | (2006.01) | |
| A61K 47/32 | (2006.01) | |
| A61K 47/34 | (2017.01) | |

(52) U.S. Cl.
CPC .......... *A61K 31/542* (2013.01); *A61K 9/0048* (2013.01); *A61K 9/08* (2013.01); *A61K 47/02* (2013.01); *A61K 47/183* (2013.01); *A61K 47/186* (2013.01); *A61K 47/26* (2013.01); *A61K 47/32* (2013.01); *A61K 47/34* (2013.01)

(58) Field of Classification Search
CPC .... A61K 31/542; A61K 47/02; A61K 47/183; A61K 47/186; A61K 47/26; A61K 47/32; A61K 47/34; A61K 9/0048; A61K 9/08
See application file for complete search history.

(56) References Cited

U.S. PATENT DOCUMENTS

2013/0065888 A1*  3/2013  Cetina-Cizmek .... A61K 9/0048
                                                                  514/226.5

FOREIGN PATENT DOCUMENTS

| EP | 2394637 | * 12/2011 |
|---|---|---|
| WO | WO-2011/067791 A2 | 6/2011 |
| WO | WO-2012/053011 A2 | 4/2012 |
| WO | WO-2013/025696 A1 | 2/2013 |

OTHER PUBLICATIONS

Aldrich et al. (http://www.triphasepharmasolutions.com/Resources/USP%20Ophthalmic%20Preparations.pdf, Aug. 28 2013). (Year: 2013).*
Written Opinion for PCT/IB2014/065806 dated Apr. 14, 2015, 5 pages.
International Search Report for PCT/IB2014/065806 dated Apr. 21, 2015, 4 pages.

* cited by examiner

*Primary Examiner* — Umamaheswari Ramachandran
(74) *Attorney, Agent, or Firm* — Sheppard Mullin Richter & Hampton LLP

(57) ABSTRACT

The present invention provides a process of manufacturing a sterile, ophthalmic pharmaceutical suspension comprising sterile active ingredient(s) such as sterile carbonic anhydrase inhibitors (CAIs) wherein the process does not involve the use of any special equipment's such as ball mill, milling bottle and/or jet mill The present process is simple, cost effective and efficient.

Figure 1:
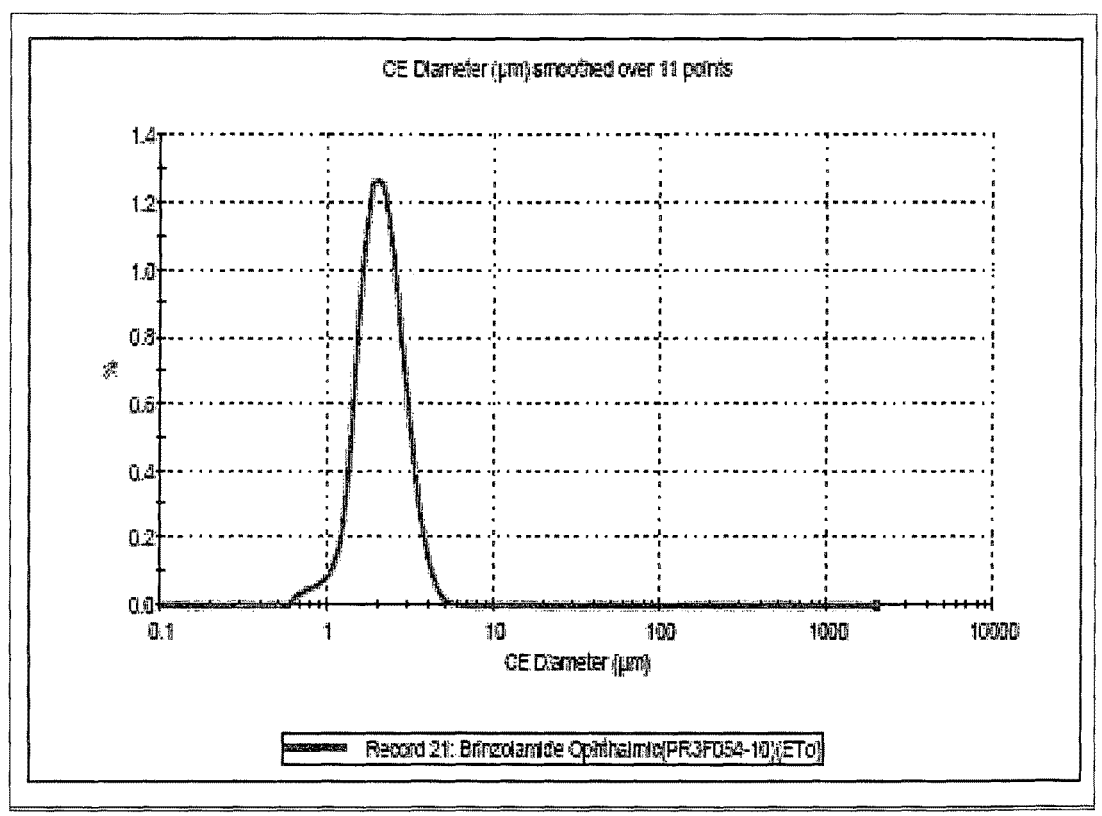

15 Claims, 2 Drawing Sheets

PROCESS FOR MANUFACTURING STERILE OPHTHALMIC PHARMACEUTICAL SUSPENSIONS

CROSS REFERENCE TO RELATED APPLICATIONS

This application is a U.S. National Stage Application under 35 U.S.C. § 371 of International Application No. PCT/IB2014/065806, filed Nov. 5, 2014, which application claims the benefit of Indian Application No. 3298/DEL/2013, filed Nov. 8, 2013, the contents of which are hereby incorporated by reference in their entirety into the present disclosure.

FIELD OF THE INVENTION

The present invention relates to an improved process of manufacturing sterile, ophthalmic pharmaceutical suspensions comprising sterile active ingredient(s) such as carbonic anhydrase inhibitors (CAIs), preferably sterile brinzolamide. The sterile ophthalmic pharmaceutical suspensions are useful in the treatment of elevated intraocular pressure in persons suffering from ocular hypertension or primary open angle glaucoma.

BACKGROUND OF THE INVENTION

Brinzolamide is a carbonic anhydrase inhibitor used to lower intraocular pressure in patients with ocular hypertension or open-angle glaucoma. Brinzolamide is chemically (R)-(+)-4-Ethylamino-2-(3-methoxypropyl)-3,4-dihydro-2H-thieno[3,2-e]-1,2-thiazine-6-sulfonamide-1,1-dioxide and has the empirical formula C12H21N3O5S3. Brinzolamide has a molecular weight of 383.5 and a melting point of about 131.deg.C.

This compound is disclosed in U.S. Pat. No. 5,378,703 (Dean, et al.). The compound is also disclosed in European patent EP 527801. U.S. Pat. No. 6,071,904 discloses processes for preparation of brinzolamide ophthalmic composition.

Brinzolamide ophthalmic suspension is developed and marketed by Alcon Laboratories Inc. in United States under the brand name AZOPT® (Brinzolamide ophthalmic suspension 1%). Brinzolamide is indicated for lowering elevated intra-ocular pressure (TOP) in patients with open-angle glaucoma or ocular hypertension (OHT).

Various methods have been disclosed in the prior for the preparation of brinzolamide ophthalmic suspension. International patent application WO 98/25620 teaches that conventional sterilization methods cannot be employed in the manufacture of suspensions comprising brinzolamide since the compound recrystallizes at autoclaving temperatures forming large needle-type crystals.

According to WO 98/25620, also dry heat sterilization is not suitable since it causes melting of the material, whereas sterilization by ethylene oxide and gamma irradiation introduces unacceptable degradation products.

EP0941094 discloses a process for making brinzolamide suspension by autoclaving of concentrated slurry of brinzolamide in milling bottle, ball milling of the hot slurry, and then adding the slurry to the rest of the ingredients.

EP2394637 discloses a process for sterilizing brinzolamide suspensions using gamma irradiation or ethylene oxide.

In these cited references procedures, the use of a typical ball milling process to reduce particle size of ophthalmic drugs in aqueous suspensions is not desirable for several reasons. Firstly, the ball-milling process and parameters must be carefully controlled in order to ensure adequate particle size reduction.

Secondly, it was found that the ball-milling process does not prevent subsequent aggregation of the drug particles in the suspension formulation. As a result, the suspension formulation may contain drag aggregates having a particle sizes above the recommended range for ophthalmic formulations. Thus, formulations prepared according to WO 98/25620 may not have the desired stability towards drug particle aggregation.

Thus, a cited reference discloses autoclaving of the slurry of brinzolamide and surfactant and further ball milling the slurry. However, the drawback associated with this method is that it requires a milling bottles in which the slurry of brinzolamide could initially be autoclaved and then ball milled for further size reduction of needle shaped crystals of brinzolamide that are formed during autoclaving leading to wastage, expensive, time consuming and non-reproducible process. Furthermore the use of expensive instruments adds to the cost of production.

The inventors of the present invention have surprisingly invented a cost effective, easily reproducible process with minimal use of equipment's and complex technology for manufacturing a sterile ophthalmic suspension comprising sterile brinzolamide wherein the process does not require the use of any specific equipment's such as ball mill, milling bottle and/or jet mill. This process ameliorates the drawbacks associated with cited references methods for preparation of brinzolamide ophthalmic suspension.

OBJECTS OF THE PRESENT INVENTION

The main object of the present invention is to provide an improved process of manufacturing a sterile, ophthalmic pharmaceutical suspension comprising a sterile therapeutic active agent or acceptable salts thereof and pharmaceutically acceptable excipients thereof.

Yet another object of the present invention is to provide a process which is simple, easily reproducible and cost effective.

Yet another object of the present invention is to provide a process for manufacturing ophthalmic pharmaceutical formulation without use of any specific equipment such as ball mill, milling bottle and/or jet mill.

Yet another object of the present invention is to provide a sterile ophthalmic pharmaceutical suspension that are useful in the treatment of elevated intraocular pressure in patients with ocular hypertension or open angle glaucoma.

SUMMARY OF THE INVENTION

The present invention provides a simple and efficient process of manufacturing a sterile brinzolamide ophthalmic suspension.

The present invention provides a process of manufacturing a sterile, ophthalmic pharmaceutical suspension comprising sterile active ingredient(s) such as sterile carbonic anhydrase inhibitors (CAIs) wherein the process doesn't involve the use of any special equipment's such as ball mill, milling bottle and/or jet mill.

Another embodiment of the present invention is to provide an efficient and economic process of manufacturing a sterile brinzolamide ophthalmic pharmaceutical suspension compared to ball milled process wherein the present improved process can minimize or prevent the suspended drug particles from forming aggregates.

Further embodiment of the present invention provides a process of manufacturing a sterile, ophthalmic pharmaceutical suspension comprising sterile active ingredient(s) such as sterile carbonic anhydrase inhibitors (CAIs) wherein the compositions are formulated optionally with a pharmaceutically acceptable preservative such that the suspension may be formulated both as a unit-dose as well as multi-dose composition.

Furthermore, in an embodiment, the manufacturing process of the present invention reduces the generation of Impurity A wherein the reduction of Impurity A will enhance the shelf-life of the product thereby increases the stability of the present invention.

Another embodiment of the present invention is to provide a process of manufacturing a sterile brinzolamide ophthalmic pharmaceutical suspension which ameliorates one or more drawbacks of the reference processes.

The sterile ophthalmic pharmaceutical suspensions of the present invention are useful in the treatment of elevated intraocular pressure in patients with ocular hypertension or open-angle glaucoma.

BRIEF DESCRIPTION OF THE ACCOMPANYING DRAWINGS

FIG. 1: Showing the particle size evaluation of present invention formulation of brinzolamide ophthalmic suspension 1.0% using Morphology G3 instrument from Malvern at Aimil Labs in Vadodara.

Figure 2:
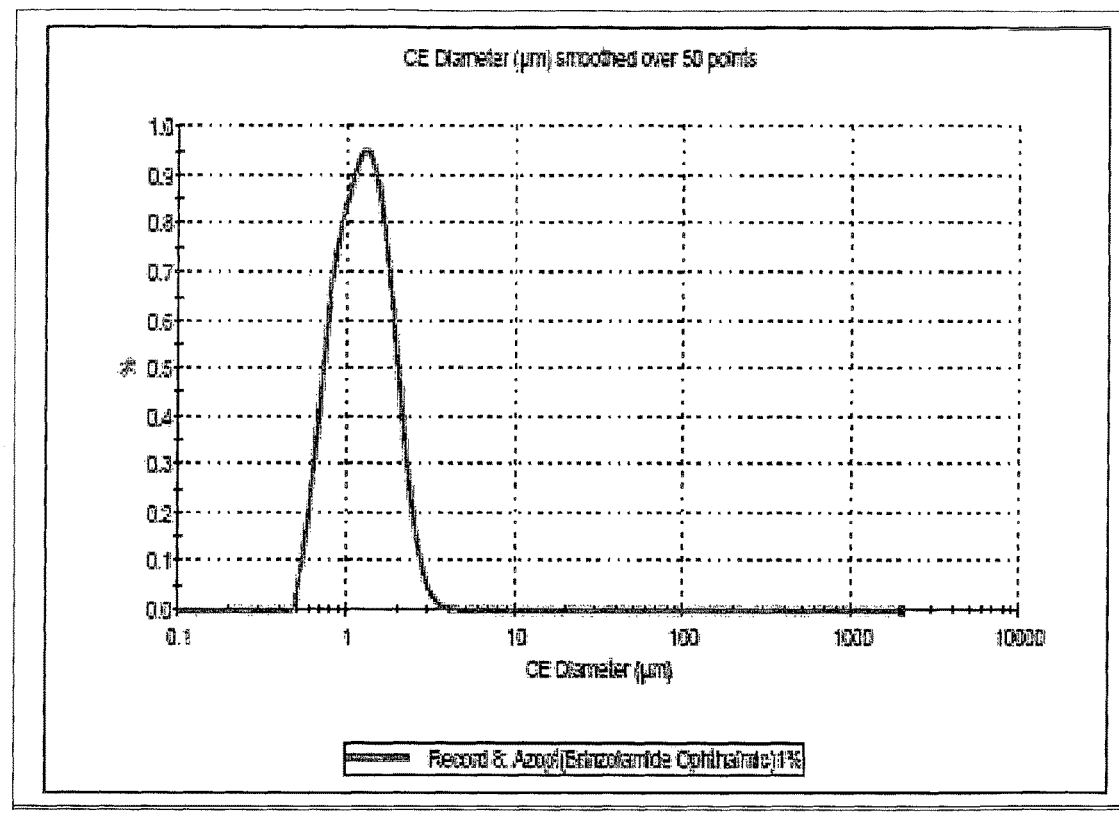

FIG. 2: Showing the particle size evaluation of Reference listed drug (AZOPT®) using Morphology G3 instrument from Malvern at Aimil Labs in Vadodara.

DETAILED DESCRIPTION OF THE INVENTION

As used herein, the term "BAC" wherever appears is an abbreviation for "benzalkonium chloride".

As used herein, the "CAIs" wherever appears is an abbreviation for "carbonic anhydrase inhibitors".

As used herein, the "brinzoalmide API" wherever appears is a sterile brinzolamide procured from ICROM S.p.A, Italy.

As used herein, the "API" wherever appears is an abbreviation for "active pharmaceutical ingredient".

As used herein, the "USP" wherever appears is an abbreviation for "United States Pharmacopeia".

As used herein, the "LDPE" wherever appears is an abbreviation for "low density polyethylene".

As used herein, the "HDPE" wherever appears is an abbreviation for "high density polyethylene".

As used herein, the "BKC" wherever appears is an abbreviation for "benzalkonium chloride".

As used herein, the "NaOH" wherever appears is an abbreviation for "Sodium Hydroxide".

As used herein, the "HCl" wherever appears is an abbreviation for "Hydrochloric Acid".

As used herein, the "EDTA" wherever appears is an abbreviation for "edetate disodium". As used herein, the "RLD" wherever appears is an abbreviation for "Reference listed drug" as developed and marketed by Alcon Laboratories Inc. in United States under the brand name AZOPT® (brinzolamide ophthalmic suspension 1%).

As used herein, wherever the drug comprises brinzolamide, the impurities preferably measured include Impurity A (S)-4-(ethylamino)-3,4-dihydro-2-(3-methoxypropyl)-2H-thieno[3,2-e]-1,2-thiazine-6-sulfonamide 1,1-dioxide; Impurity B, (R)-4-(amino)-3,4-dihydro-2-(3-methoxypropyl)-2H-thieno[3,2-e]-1,2-thiazine-6-sulfonamide 1,1-dioxide, Impurity C (S)-4-(hydroxy)-3,4-dihydro-2-(3-methoxypropyl)-2H-thieno[3,2-e]-1,2-thiazine-6-sulfonamide 1,1-dioxide and Impurity D 6-(amino-hydroxy-oxo-6-sulfanyl)-2-(3-methoxypropyl)-1,1-dioxo-3H-thieno[3,2-e]thiazin-4-one. As used herein, the "active ingredient" is defined as the chemical substance, which is used in the prevention or treatment of various diseases associated with human or non-human animals.

The present invention relates to an improved process of manufacturing a sterile ophthalmic pharmaceutical suspension of sterile active ingredient(s) such as sterile carbonic anhydrase inhibitor (CAI) or combinations thereof.

The term sterile active ingredient(s) can be interchangeably used with their pharmaceutically acceptable salt(s), hydrate(s), solvate(s), polymorph(s), stereoisomers), ester(s), prodrug(s), complex(es) and their metabolites thereof.

According to one embodiment of the present invention there is provided a sterile ophthalmic suspension prepared by the process as described herein comprising sterile brinzolamide in an amount from 0.001% to 5.0% by weight.

In an embodiment of the present invention there is provided an improved process of manufacturing a sterile ophthalmic suspension wherein the process comprising the steps of:
  a) preparing a solution comprising polymer (Carbomer(R) 974 P), chelating agent (edetate disodium), one or more tonicity agents (mannitol and/or sodium chloride) and optionally with a preservative (benzalkonium chloride).
  b) adjusting the pH of the solution of step a) between 7.5±0.3 by adding sodium hydroxide/hydrochloric acid, in increments, if required.
  c) sterilizing the bulk of step a) by in-situ sterilization.
  d) preparing a surfactant (Tyloxapol(R) or Triton X-100 (R)) solution in another pressure vessel.
  e) filtering a surfactant solution of step d) through 0.2 µ filter.
  f) adding aseptically sterile API to the above surfactant solution of step e).
  g) homogenizing the above slurry using high pressure homogenizer at pressure 1000±200 bar to achieve uniform dispersion.
  h) transferring this homogenized slurry into sterile bulk in filtration tank of step c).
  i) Continue the stirring to get a uniform bulk.
  Volume makeup with water for injection.

Another embodiment of the present invention is to provide an improved process for preparation of sterile brinzolamide ophthalmic suspension, the process being efficient, economic, and feasible for commercial scale preparation and which does not involve the use of any special equipment's such as ball mill, milling bottle and/or jet mill.

In another embodiment of the present invention is to provide a process of manufacturing a sterile brinzolamide ophthalmic pharmaceutical suspension which ameliorates one or more drawbacks of the cited references processes.

In one of the preferred embodiment the present inventors uses approximately only $1/10^{th}$ of the batch volume for high pressure homogenization at pressure 1000±200 bar whereas the innovator uses the entire batch for ball milling. Thus the process of present invention leads to the minimal wastage of batch product. Also there are no viscosity issues in the product of present invention with the use of carbomer which further leads to easily homogenisable product which is easy to process and handle.

According to a preferred embodiment, the present invention provides a sterile brinzolamide ophthalmic suspensions comprising: the sterile active ingredient brinzolamide, tyloxapol(R); Carbomer(R) 974 P; mannitol, sodium chloride, edetate disodium, benzalkonium chloride, sodium hydroxide and/or hydrochloric acid (to adjust the pH) wherein the process does not involve the use of any special equipment's such as ball mill, milling bottle and/or jet mill.

According to a another preferred embodiment, the present invention provides a sterile ophthalmic suspensions comprising: the sterile active ingredient brinzolamide, tyloxapol (R); Carbomer(R) 974 P; mannitol, sodium chloride, edetate disodium, sodium hydroxide and/or hydrochloric acid (to adjust the pH) wherein the process does not involve the use of any special equipment's such as ball mill, milling bottle and/or jet mill.

The active ingredient used in the pharmaceutical ophthalmic suspension, may be a soluble or sparingly soluble or slightly soluble or very slightly soluble or practically insoluble compound(s) selected from the group but are not limited to a carbonic anhydrase inhibitor (CAI), such as sterile brinzolamide, acetazolamide, dorzolamide, methazolamide; a beta-blocker, such as timolol, arteolol, metopranolol, betaxolol or other actives used for ophthalmic formulation or a pharmaceutically acceptable salt(s), hydrate(s), solvate(s), polymorph(s), stereoisomers), ester(s), prodrug(s), complex(es) and their metabolites thereof. One of the preferred active is a CAI, or a beta-blocker or a steroid. In a preferred embodiment the CAI is brinzolamide which is sterile in nature, can be in combination with a beta-blocker.

Brinzolamide API used in the preparation of pharmaceutical suspension of the present invention is a sterile brinzolamide procured from ICROM S.p.A, Italy.

Examples of polymers that may be used according to the invention include, but are not limited to Carbomer(R) such as Carbomer(R) 974 P (a synthetic, high molecular weight crosslinked polymer of acrylic acid), povidone, hydroxypropylmethylcellulose, hydroxypropylcellulose, hydroxyethylcellulose and mixtures thereof. Polymers may be used in amount from about 0.1% to about 5.0%, preferably from about 0.3% to about 1.0%.

Examples of preservatives that may be used according to the invention include but are not limited to quaternary ammonium salts such as benzalkonium chloride (BKC) and benzethonium chloride; cationic compounds such as chlorhexidine gluconate; p-hydroxybenzoates such as methyl p-hydroxybenzoate, ethyl p-hydroxybenzoate, propyl p-hydroxybenzoate and butyl p-hydroxybenzoate; alcohol compounds such as chlorobutanol and benzyl alcohol; sodium dehydroacetate; and thiomersal, benzethonium chloride, phenyl ethanol, phenyl propanol, phenyl mercuric acetate, phenyl mercuric nitrate, phenyl mercuric borate, chlorhexidine acetate or gluconate, cetrimide, chlorocresol, sodium methyl paraben, sodiumpropyl paraben, thimerosal, benzalkonium chloride and mixtures thereof and may be used in an amount from about 0.001% to about 0.5%, preferably from about 0.005% to about 0.05%. Of the recited preservatives, quaternary ammonium salts and cationic compounds are preferable as they suppress formation of agglomerates, prevent lowering of pH, and provide a suspension superior in redispersibility and stability. Of the quaternary ammonium salts, benzalkonium chloride and benzethonium chloride are particularly preferable, and chlorhexidine gluconate is particularly preferable as the cationic compound.

Examples of surfactants that may be used according to the invention include but are not limited to Tyloxapol(R), Triton X-100(R), polysorbates, polyoxyl 35 castor oil, polyoxyl 40 hydrogenated castor oil, polyoxyl 40 stearates, sorbitan monolaureates, poloxamer and mixtures thereof and may be used in amount from about 0.001% to about 15%, preferably from about 0.01% to about 0.5%. Tyloxapol(R) is chemically known as 4-(1,1,3,3-Tetramethylbutyl)phenol polymer with formaldehyde and oxirane. Triton X-100(R) is chemically known as (a-[4-(1,1,3,3-tetramethylbutyl)phenyl]-co-hydroxypolyoxy-1,2-ethane diyl).

The surfactants used in the pharmaceutical ophthalmic suspension for enhancing dispersion stability preferably include nonionic surfactant(s). The nonionic surfactant to be used is nontoxic, non-irritant and applicable to the eye. Non-limiting examples of the nonionic surfactant include but are not limited to polymer of the alkyl aryl polyether alcohol like tyloxapol; polyoxyethylene polyoxypropylene polymer like triton X-100; polyoxyethylenesorbitan fatty acid esters such as polyoxyethylenesorbitan monooleate, polyoxyethylenesorbitan monolaurate, polyoxyethylenesorbitan monopalmitate and polyoxyethylenesorbitan monostearate; polyoxyethylene hydrogenated castor oils; sorbitan fatty acid esters such as sorbitan monooleate, sorbitan monolaurate, sorbitan monopalmitate and sorbitan monostearate; polyoxyethylene alkyl ethers such as polyoxyethylene lauryl ether; and polyoxyethylene fatty acid esters such as polyoxyethylene monostearate and mixtures thereof. Of the recited nonionic surfactants, alkyl aryl polyether alcohol like tyloxapol, polyoxyethylene polyoxypropylene polymer like triton X-100 are preferable, since they suppress formation of agglomerates, prevent lowering of pH, and provide a suspension superior in redispersibility and stability. The nonionic surfactant is generally contained in a proportion of from about 0.005 w/v % to about 1.0 w/v %, preferably from about 0.01 to about 0.5 w/v % and more preferably from about 0.05 w/v % to about 0.3 w/v % relative to the entire suspension.

Examples of tonicity agents that may be used according to the invention include but are not limited to mannitol, dextrose, glycerin, potassium chloride, sodium chloride and mixtures thereof. The tonizing agent is added in such an amount that makes the osmotic pressure of the suspension identical to that of tears, preferably tonicity agents may be used in amount from about 1% to about 5%.

The pharmaceutical ophthalmic suspension may further include a buffer. The buffer should have buffering capacity in the range of pH from about 5.0 to about 9.0. Examples of the buffer include but are not limited to acetates such as sodium acetate; phosphates such as sodium dihydrogenphosphate, disodium hydrogenphosphate, potassium dihydrogenphosphate and dipotassium hydrogenphosphate; .epsilon.-aminocaproic acid; amino acid salts such as sodium glutamate; and boric acid and a salt thereof. Of the mentioned buffers, acetates and .epsilon.-aminocaproic acid are preferable as they suppress formation of agglomerates, prevent lowering of pH, and provide a suspension superior in re-dispersibility and stability. The buffer is generally contained in a proportion of form about 0.01 w/v % to about 2.0 w/v %, preferably form about 0.05 w/v % to about 0.5 w/v % relative to the entire suspension.

Examples of the pH adjusting agent include but are not limited to hydrochloric acid, citric acid, phosphoric acid, acetic acid, tartaric acid, sodium hydroxide, potassium hydroxide, sodium carbonate and sodium hydrogen carbonate. The pharmaceutical ophthalmic suspension is generally adjusted to pH from about 5.0 to about 9.0, the range which is less irritating to the mucosal membrane of the eye.

Suitable chelating agents include but are not limited to edetate disodium, edetate trisodium, edetate tetrasodium, diethyleneamine pentaacetate and mixtures thereof. Most preferred is edetate disodium. The chelating agent is generally present in an amount from about 0.001 w/v % to about 0.1 w/v % relative to the entire suspension. In the case of edetate disodium, the chelating agent is preferably present at a concentration of from about 0.005 w/v % to about 0.05 w/v % relative to the entire suspension.

Examples of the antioxidant include but are not limited to ascorbic acid, sodium ascorbate, tocopherol and sulfite salts like sodium sulfite, potassium sulfite, magnesium sulfite, calcium sulfite, sodium bisulfite, potassium bisulfite, magnesium bisulfite, calcium bisulfite, sodium metabisulfite, potassium metabisulfite, calcium metabisulfite, sodium thiosulfate and sodium hydrogensulfite. The sulfite salt is generally being present in an amount from about 0.01 w/v % to about 1% w/v % relative to the entire suspension.

The average particle size of the dispersed or the suspended active is generally from about 0.01 μ-to about 50 μ, preferably from about 0.01 μ-to about 30 μ, more preferably from about 0.1 μ-to about 20 μ and most preferably from about 0.1 μ-to about 5.0 μ. The use of the active in this particle size range affords a suspension having superior dispersibility, which is less irritating to the mucosal membrane of the eye.

Any pharmaceutically acceptable packaging material may be use, preferably packaging material that is suitable for containing ophthalmic pharmaceutical suspensions.

The ophthalmic pharmaceutical suspension is preferably sterile. An article comprising the ophthalmic pharmaceutical suspension filled in a container is preferably sterile, preferably at the time the container is filled. The ophthalmic pharmaceutical suspension is preferably filled into sterile multi-use or single-use containers.

Pharmaceutically acceptable packaging materials include but are not limited to low density polyethylene ("LDPE"), high density polyethylene ("HDPE"), polypropylene, polystyrene, polycarbonate, polyesters (such as polyethylene terephthalate and polyethylene naphthalate), nylon, polyvinyl chloride), poly(vinylidine chloride), poly(tetrafluoroethylene) and other materials known to those of ordinary skill in the art. Flexible bottles prepared from, or comprising, LDPE, HDPE or polypropylene are particularly preferred.

In another embodiment of the present invention, the homogenized ophthalmic suspension of sterile brinzolamide prepared according to the process as described herein may be filled in three piece low density polyethylene bottle (LDPE), of suitable capacity in volumes of 2.5 ml, 5 ml, 10 ml and 15 ml plugged with natural (LDPE) nozzle and seal with orange colored high density polyethylene (HDPE) cap.

Any suitable method can be used to sterilize the containers, and can be determined by the person of ordinary skill in the art. Some preferred methods include exposure to gamma irradiation and/or exposure to ethylene oxide gas.

The present invention provides a method of using the ophthalmic pharmaceutical formulation for treating ocular hypertension and glaucoma.

The preferred active ingredient includes but are not limited to the active which is useful in the treatment or prevention of diseases associated to eye like elevated intraocular pressure in patients with ocular hypertension or open-angle glaucoma, ocular surface pain, uveitis, scleritis, episcleritis, keratitis, surgically-induced inflammation, endophthalmitis, iritis, atrophic macular degeneration, retinitis pigmentosa, iatrogenic retinopathy, retinal tears and holes, cystoid macular edema, diabetic macular edema, diabetic retinopathy, sickle cell retinopathy, retinal vein and artery occlusion, optic neuropathy, exudative macular degeneration, neovascular glaucoma, corneal neovascularization, cyclitis, sickle cell retinopathy, pterygium, seasonal allergic conjunctivitis, palpebral and bulbar conjunctiva, acne rosacea, superficial punctuate keratitis, herpes zoster keratitis, iritis, cyclitis, selected infective conjunctivitides, post-operative inflammation following ocular surgery.

The main embodiment of the present invention provides an improved process of manufacturing a sterile, ophthalmic pharmaceutical suspension comprising a sterile active ingredient, at least one surfactant, wherein the said process comprises steps of:
  i. subjecting a suspension of the sterile active ingredient in an aqueous solution of surfactant to homogenization to form a mixture; and,
  ii. combining the mixture formed in step (a) with the rest of the inactive ingredients, wherein inactive ingredients comprises of:
     a) at least one polymer(s),
     b) at least one or two tonicity agent(s) or combinations thereof, and
     c) optionally a pharmaceutically acceptable preservative; wherein the process doesn't involve the use of any special equipment's such as ball mill, milling bottle and/or, jet mill to achieve desired particle size.

In another embodiment of the present invention, the sterile active ingredient is a sterile carbonic anhydrase inhibitor.

In another embodiment of the present invention, the sterile carbonic anhydrase inhibitor is sterile brinzolamide.

In another embodiment of the present invention, the manufacturing process reduces the generation of Impurity A.

In another embodiment of the present invention, the ophthalmic pharmaceutical suspension upon storage for 3 months, comprises less than 0.4 w/v % of Impurity A (S)-4-(ethylamino)-3,4-dihydro-2-(3-methoxypropyl)-2H-thieno[3,2-e]-1,2-thiazine-6-sulfonamide 1,1-dioxide.

In another embodiment of the present invention, wherein the surfactant is selected from the group consisting of Tyloxapol(R), Triton X-100(R), polysorbates, polyoxyl 35 castor oil, polyoxyl 40 hydrogenated castor oil, polyoxyl 40 stearates, sorbitan monolaureates, poloxamer and the mixture thereof.

In another embodiment of the present invention, wherein the polymer is selected from the group consisting of Carbomer(R), povidone, hydroxypropyl methyl cellulose, hydroxypropyl cellulose, hydroxyethyl cellulose and the mixture thereof.

In another embodiment of the present invention, wherein the preservative is selected from the group consisting of benzethonium chloride, phenyl ethanol, phenyl propanol, phenyl mercuric acetate, phenyl mercuric nitrate, phenyl mercuric borate, chlorhexidine acetate or gluconate, cetrimide, chlorocresol, sodium methyl paraben, sodiumpropyl paraben, thimerosal, benzalkonium chloride and the mixture thereof.

In another embodiment of the present invention, wherein the tonicity agents are selected from the group consisting of mannitol, dextrose, glycerin, potassium chloride, sodium chloride and the mixture thereof.

In another embodiment of the present invention, wherein the chelating agents if used, include edetate disodium, edetate trisodium, edetate tetrasodium, diethyleneamine pentaacetate and the mixture thereof.

In another embodiment of the present invention, the homogenization is carried out by using high pressure homogenization at pressure 1000±200 bar for uniform dispersion.

In another embodiment of the present invention, the process does not involve the use of any special equipment's such as ball mill, milling bottle and/or jet mill.

Yet another embodiment of the present invention provides a sterile, ophthalmic pharmaceutical suspension as prepared by the claimed process of manufacturing.

Yet another embodiment of the present invention provides a process of manufacturing a sterile, ophthalmic pharmaceutical suspension comprising a carbonic anhydrase inhibitor (CAI), which comprises the steps of:
 a) preparing a solution comprising polymers, chelating agents, one or more tonicity agents and optionally a pharmaceutically acceptable preservative.
 b) adjusting the pH of the solution of step a) between 7.5±0.3 by adding sodium hydroxide/hydrochloric acid, in increments, if required.
 c) sterilizing the bulk of step a) by in-situ sterilization.
 d) preparing a surfactant solution in another pressure vessel.
 e) filtering a surfactant solution of step d) through 0.2 μ filter.
 f) adding aseptically sterile API to the above surfactant solution of step e).
 g) homogenizing the above slurry using high pressure homogenizer at pressure 1000±200 bar to achieve uniform dispersion.
 h) transferring this homogenized slurry into sterile bulk in filtration tank of step c).

In another embodiment of the present invention, the ophthalmic pharmaceutical suspension is stable when stored for 3 months at 40° C. at no more than 25% relative humidity.

In another embodiment of the present invention, the ophthalmic pharmaceutical suspension is packaged in a multi dose container.

In another embodiment of the present invention, the ophthalmic pharmaceutical suspension is packaged in a unit dose container.

Yet another embodiment of the present invention provides a sterile, ophthalmic pharmaceutical suspension as prepared by the claimed process of manufacturing.

In another embodiment of the present invention, wherein the ophthalmic pharmaceutical suspension is used for treating elevated intraocular pressure in persons suffering from ocular hypertension or primary open angle glaucoma, comprising applying once a day to an eye of a patient in need thereof.

In another embodiment of the present invention, the applying of ophthalmic solution is done twice a day.

In another embodiment of the present invention, the applying of ophthalmic solution is done at least once a day.

Stability Studies:

A sterile, ophthalmic pharmaceutical suspension of the present invention is prepared by the process described herein in the specification and is tested for stability against a control product (herein referred to as "AZOPT®"). Three (3) months accelerated testing refers to storage at 40° C., at not more than 25% relative humidity (RH). Results for 3-months accelerated testing for both the control product (herein referred to as "AZOPT®") and the present invention formulation are provided in Table 1.

An accelerated study comprises placing the composition/suspension is filled in 10 mL 3 piece natural LDPE bottles, natural LDPE nozzle and orange colored cap. (Sterilized by ETO gas Sterilization) and maintaining at 40° C., at not more than 25% relative humidity (RH) in the dark.

As understood by those of skill in the art, when the drug comprises brinzolamide, the impurities preferably measured include Impurity A (S)-4-(ethylamino)-3,4-dihydro-2-(3-methoxypropyl)-2H-thieno[3,2-e]-1,2-thiazine-6-sulfonamide 1,1-dioxide; Impurity B, (R)-4-(amino)-3,4-dihydro-2-(3-methoxypropyl)-2H-thieno[3,2-e]-1,2-thiazine-6-sulfonamide 1,1-dioxide, Impurity C (S)-4-(hydroxy)-3,4-dihydro-2-(3-methoxypropyl)-2H-thieno[3,2-e]-1,2-thiazine-6-sulfonamide 1,1-dioxide and Impurity D 6-(amino-hydroxy-oxo-6-sulfanyl)-2-(3-methoxypropyl)-1,1-dioxo-3H-thieno[3,2-e]thiazin-4-one and total impurities, as well as identification of the amount of the any independent unspecified impurity.

TABLE 1

Comparative Stability Data of "Reference listed drug" AZOPT$^{(R)}$ and present invention formulation.

| Batch No. | Release | | Shelf life | 40° C./25% RH | |
|---|---|---|---|---|---|
| Assay | Specifications | Initial | Specifications | 1 Month | 3 Months |
| RLD (AZOPT$^{(R)}$) B. No. 203168F | 93.0-107.0% of labeled amount | 98.6% | 90.0-110.0% of labeled amount | 100.2% | 100.7% |
| Exhibit batch E14010 | | 97.8% | | 99.4% | 99.5% |
| Impurity Related compound A (Impurity A) | | | | | |
| RLD (AZOPT$^{(R)}$) B. No. 203168F | NMT 1.0% | 0.91% | NMT 1.5% | 0.96% | 1.39% |
| Exhibit batch E14010 Related compound B (Impurity B) | | ND | | 0.08% | 0.25% |
| RLD (AZOPT$^{(R)}$) B. No. 203168F | NMT 0.4% | 0.05% | NMT 0.5% | 0.05% | 0.04% |
| Exhibit batch E14010 | | 0.13% | | 0.15% | 0.17% |

TABLE 1-continued

Comparative Stability Data of "Reference listed drug" AZOPT(R) and present invention formulation.

| Batch No. | Release | | Shelf life | 40° C./25% RH | |
|---|---|---|---|---|---|
| Assay | Specifications | Initial | Specifications | 1 Month | 3 Months |
| Related compound D (Impurity D) | | | | | |
| RLD (AZOPT(R)) B. No. 203168F | NMT 0.4% | ND | NMT 0.5% | ND | ND |
| Exhibit batch E14010 | | 0.01% | | ND | 0.02% |
| Any individual impurity | | | | | |
| RLD (AZOPT(R)) B. No. 203168F | NMT 0.4% | 0.08% | NMT 0.5% | 0.10% | 0.18% |
| Exhibit batch E14010 | | 0.11% | | 0.14% | 0.15% |
| Total impurities | | | | | |
| RLD (AZOPT(R)) B. No. 203168F | NMT 1.0% | 0.12% | NMT 2.0% | 0.15% | 0.35% |
| Exhibit batch E14010 | | 0.25% | | 0.29% | 0.34% |

As used herein, the "NMT" wherever appears is an abbreviation for "Not more than".

As used herein, the "ND" wherever appears is an abbreviation for "Not detected".

Details of the Batches:

| Batch No. | Mfg. date/Expiry date | Date of initiation of study |
|---|---|---|
| Exhibit batch E14010 | Mfg. date: May 14 | 31 May 14 |
| RLD (AZOPT(R)) B. No. 203168F manufactured by Alcon Laboratories Inc. | Exp. Date: Mar 14 | 29 Nov 13 |

TABLE 2

Comparative data of different lots of RLD from different markets

| | Russia RLD | EU RLD | US RLD | | |
|---|---|---|---|---|---|
| Batch No. | 13F21F | 12F19G | 203411F | 203168F | 231374F |
| Expiry date | Jun 15 | May 14 | Apr 14 | Mar 14 | May 16 |
| Date of analysis | Nov 13 | Nov 13 | May 13 | Nov 13 | Sep 14 |
| Approximate age of the product at the time of analysis | 5 months* | 1.5 years* | 1 year* | 1.7 year* | 4 months* |
| Assay (By HPLC) | 98.90% | 100.50% | 102.00% | 98.58% | 97.30% |
| Related compound A (Impurity A) | 0.86% | 0.60% | 0.90% | 0.91% | 0.75% |
| Impurity B | 0.05% | 0.04% | 0.05% | 0.05% | 0.05% |
| Impurity D | ND | ND | ND | ND | 0.01% |
| Any individual impurities | 0.07% | 0.13% | 0.04% | 0.08% | 0.32% |
| Total impurity | 0.12% | 0.24% | 0.22% | 0.13% | 0.38% |

*Approximate age of the product at the time of analysis based on anticipated two (2) years of shelf life.

Observations:

It is observed from the stability data that due to an improved process, formation of related substance A (Impurity A) at initial time point is much less in present invention formulation than RLD (AZOPT®) due to which its formation over the time at accelerated condition has decreased.

In case of RLD, the impurity A has increased from 0.91% (at initial) to 1.39% in three (3) months at accelerated condition whereas in case of present invention formulation the impurity was not detected at initial analysis and has increased to 0.25% over three (3) months at same condition indicating that the rate of increase of impurity A has decreased by exactly half in case of present invention formulation due to an improved process.

The impurity A of RLD is more than the present invention formulation whether the analysis is done near to the expiry of the RLD or one (1) year before its expiry, as it can be seen from the table that initial assay of impurity A is not correlating well with the age of the product. This supports the statement that manufacturing process is a main contributor for the formation of impurity A. Impurity A is also formed on stability. However controlling Impurity A by manufacturing process gives a better control over it.

Some other parameters like content of BKC, content of Edetate Disodium, Osmolality, Viscosity, pH and Particle Size were also analyzed and were found to be within specifications and comparable with the RLD.

Conclusion:

From the above stability results it can be easily concluded that the present invention formulation complies with the specifications as per USP and in-house specification throughout the study and is comparable with the RLD.

It is also concluded that the present invention formulation is more stable over the period of three (3) months at accelerated condition (40±2° C./25%RH) and stability data is well within the specifications and comparable with the RLD (AZOPT®). Hence the present invention formulation prepared by the improved process is more patient compliant.

Further, it is also concluded that the manufacturing process of the present invention reduces the generation of Impurity A wherein the reduction of Impurity A will enhance the shelf-life of the product thereby increases the stability of the present invention.

Furthermore, the ophthalmic pharmaceutical suspension of the present invention upon storage for 3 months, comprises less than 0.4 w/v % of Impurity A (S)-4-(ethylamino)-3,4-dihydro-2-(3-methoxypropyl)-2H-thieno[3,2-e]-1,2-thiazine-6-sulfonamide 1,1-dioxide.

Zeta Potential

The Study was done in the Malvern Application Laboratory (Delhi) which is a joint venture between Malvern Instruments (UK), a particle characterization and Rheological instrumentation manufacturer, and Aimil Ltd (India), "India's leading civil engineering instrumentation manufacturer". Malvern's Zetasizer ZS90 was used for the study.

Zeta potential was determined from three (3) Azopt (RLD) batches, 2 batches made in In-house lab and a placebo batch. Due to the high viscosity of the formulation, it was very difficult to measure the zeta potential. So zeta potential was determined for all the above batches after diluting 10 times. The results are shown in the Table 5.

TABLE 5

Zeta potential data of In-house batches and RLD

| Batch No. | Mfg. date | Measured after 10 times dilution |
| --- | --- | --- |
| PR3F054-18B (Present invention) | Jul. 13, In-house Lab | −34.5 |
| PR3F054-10 (Present invention) | May 13, In-house Lab | −32.7 |
| 203411F (Azopt) | Alcon USA (Exp.- April 2014) | −33.9 |
| 12F19G (Azopt) | Alcon, UK (Exp.- May 2014) | −31.9 |
| PR3F054-35P (Placebo) | Oct. 13, In-house Lab | −35.8 |

Inference:

Based on the above data, the zeta potential for Sentiss batches and Azopt were similar and there was no significant difference between them. Further, high negative value of placebo is indicative of high viscosity with high polymeric cross links. Hence, suspension stability is maintained by high polymeric network and not by electric charge. The present invention is further illustrated by reference to the following examples which is for illustrative purpose only and does not limit the scope of the invention in any way.

EXAMPLES

The scope of the present invention is illustrated by the following examples which are not meant to restrict the scope of the invention in any manner whatsoever.

The term 'q.s.' wherever appears in the examples is an abbreviation for 'quantity sufficient' which is the amount of the excipient in such quantities that is just sufficient for its use in the composition of the present invention.

Example 1

| Ingredients | Quantity (%) |
| --- | --- |
| Brinzolamide | 1 |
| Tyloxapol | 0.025 |
| Carbomer 974P | 0.45 |
| Edetate disodium | 0.01 |
| BKC | 0.01 |
| Mannitol | 3.3 |
| Sodium Chloride | 0.25 |
| NaOH/HCl | q.s. |
| Water for Injection | Up to 100% |

Example 2

| Ingredients | Quantity (%) |
| --- | --- |
| Brinzolamide | 1.0 |
| Tyloxapol | 0.025 |
| Carbomer 974P | 0.42 |
| Edetate disodium | 0.01 |
| Benzalkonium Chloride | 0.01 |
| Mannitol | 3.3 |
| Sodium chloride | 0.25 |
| Sodium hydroxide/Hydrochloric acid | q.s. |
| Water for Injection | q.s. |

Brief Manufacturing Procedure:

The process for preparation of pharmaceutical ophthalmic suspension shall be divided in following parts.
1. Remaining product vehicle (solution of EDTA, Mannitol, Carbomer, sodium chloride, Benzalkonium chloride) (37 kg)
2. Tyloxapol solution/API slurry
3. Slurry Homogenization (by mixing Tyloxapol solution)
4. Water for injection.

Part A. Remaining Product Vehicle:
5. Weigh and check the weight of all ingredients.
6. Take approximately 120% of required quantity of Water for injection in a Manufacturing tank-1
7. Purge filtered Nitrogen gas and Cool Water for Injection, using cooling jacket to 30° C. (range 25° to 35° C.), through sparger till the dissolved oxygen level reaches to not more than 2 ppm.
8. Transfer 60% of required quantity of cooled water for injection from manufacturing tank-1 to Manufacturing tank-2.
9. Add and dissolve edetate disodium in the Manufacturing tank-2 with continuous stirring.
10. Add and dissolve Mannitol in the Manufacturing tank-2 with continuous stirring
11. Add and dissolve carbomer 974P slowly in the Manufacturing tank-2 with continuous stirring.
12. Add and dissolve sodium chloride in the Manufacturing tank-2 with continuous stirring at RPM 350±50.
13. Add and dissolve diluted Benzalkonium chloride solution in the Manufacturing tank-2 with continuous stirring. Rinse the container multiple times with sufficient water for injection for complete transfer.
14. Adjust the pH of the solution between 7.5±0.3 by adding 5 N Sodium Hydroxide/1N Hydrochloric Acid, in increments, if required. Stir solution for 5 min between each increment.
15. Make up the weight of bulk solution to 37 kg.
16. Transfer the above bulk solution from manufacturing tank-2 to filtration tank through 20 µ Polypropylene filter. Record the loss during transfer.
17. Sterilize the bulk in filtration tank by in-situ sterilization (30 min, NLT 121.6° C., 1 cycle)

Part B. Tyloxapol Solution
18. In separate pressure vessel prepare the solution of Tyloxapol by collecting 3-4 L water for injection in pressure vessel and dissolve the dispensed batch quantity in hot water for injection and adding this to pressure vessel. Make up the volume to 10% of batch size.
19. Filter this solution through 0.2 μ filter into filtration area (5 L tank).

Part C. Slurry Homogenization (by Mixing Tyloxapol Solution)
20. Add aseptically sterile API to the above tyloxapol solution.
21. Stir the slurry for not less than 3 hr using magnetic stirrer at sufficient RPM to generate vortex and avoiding high turbulence.
22. Create loop to facilitate the recirculation in homogenization process and its transfer to filtration tank. Homogenize the slurry using high pressure homogenizer at pressure 1000±200 bar for 2 hr (for 50 L batch size)
23. Transfer this homogenized slurry into sterile bulk in filtration tank.
24. Rinse the slurry tanks (5 L tank) with aseptically filtered, approximately 5 L water (Refer Part D for details) and add this rinsate to sterile bulk in filtration tank through homogenizer (at pressure 1000±200 bar)
25. Make the bulk weight considering density 1.016 g/ml in filtration tank using sterile water for injection. used in rinsing of 5 L tank.
26. Continue the stirring to get a uniform bulk. Stir it for 2 hr and send the samples for bulk analysis.

Part D: Pre-Sterilized Water for Injection
27. Collect water for injection into manufacturing tank 1, filter it through 0.2 μ filter, used for filtering tyloxapol solution & collect in 5 L tank (used for slurry) and use this for volume make up in filtration tank.

Example 3

| Ingredients | Quantity (%) |
| --- | --- |
| Brinzolamide | 1.0 |
| Tyloxapol | 0.025 |
| Carbomer 974P | 0.42 |
| Edetate disodium | 0.01 |
| Mannitol | 3.3 |
| Sodium chloride | 0.25 |
| Sodium hydroxide/Hydrochloric acid | q.s. |
| Water for Injection | q.s. |

Brief Manufacturing Procedure:
The process for preparation of pharmaceutical ophthalmic suspension shall be divided in following parts.
1. Remaining product vehicle (solution of EDTA, Mannitol, Carbomer, sodium chloride)
2. Tyloxapol solution/API slurry
3. Slurry Homogenization (by mixing Tyloxapol solution)
4. Water for injection.

Part A. Remaining Product Vehicle:
5. Weigh and check the weight of all ingredients.
6. Take approximately 120% of required quantity of Water for injection in a Manufacturing tank-1
7. Purge filtered Nitrogen gas and Cool Water for Injection, using cooling jacket to 30° C. (range 25° to 35° C.), through sparger till the dissolved oxygen level reaches to not more than 2 ppm.
8. Transfer 60% of required quantity of cooled water for injection from manufacturing tank-1 to Manufacturing tank-2.
9. Add and dissolve edetate disodium in the Manufacturing tank-2 with continuous stirring.
10. Add and dissolve Mannitol in the Manufacturing tank-2 with continuous stirring
11. Add and dissolve carbomer 974P slowly in the Manufacturing tank-2 with continuous stirring.
12. Add and dissolve sodium chloride in the Manufacturing tank-2 with continuous stirring at RPM 350±50.
13. Rinse the container multiple times with sufficient water for injection for complete transfer.
14. Adjust the pH of the solution between 7.5±0.3 by adding 5 N Sodium Hydroxide/1 N Hydrochloric Acid, in increments, if required. Stir solution for 5 min between each increment.
15. Make up the weight of bulk solution to 37 kg.
16. Transfer the above bulk solution from manufacturing tank-2 to filtration tank through 20 μ Polypropylene filter. Record the loss during transfer.
17. Sterilize the bulk in filtration tank by in-situ sterilization (30 min, NLT 121.6° C., 1 cycle)

Part B. Tyloxapol Solution
18. In separate pressure vessel prepare the solution of Tyloxapol by collecting 3-4 L water for injection in pressure vessel and dissolve the dispensed batch quantity in hot water for injection and adding this to pressure vessel. Make up the volume to 10% of batch size.
19. Filter this solution through 0.2 μ filter into filtration area (5 L tank).

Part C. Slurry Homogenization (by Mixing Tyloxapol Solution)
20. Add aseptically sterile API to the above tyloxapol solution.
21. Stir the slurry for not less than 3 hr using magnetic stirrer at sufficient RPM to generate vortex and avoiding high turbulence.
22. Create loop to facilitate the recirculation in homogenization process and its transfer to filtration tank. Homogenize the slurry using high pressure homogenizer at pressure 1000±200 bar for 2 hr (for 50 L batch size)
23. Transfer this homogenized slurry into sterile bulk in filtration tank.
24. Rinse the slurry tanks (5 L tank) with aseptically filtered, approximately 5 L water (Refer Part D for details) and add this rinsate to sterile bulk in filtration tank through homogenizer (at pressure 1000±200 bar)
25. Make the bulk weight considering density 1.016 g/ml in filtration tank using sterile water for injection. used in rinsing of 5 L tank.
26. Continue the stirring to get a uniform bulk. Stir it for 2 hr and send the samples for bulk analysis.

Part D. Pre-Sterilized Water for Injection
27. Collect water for injection into manufacturing tank 1, filter it through 0.2 μ filter, used for filtering tyloxapol solution & collect in 5 L tank (used for slurry) and use this for volume make up in filtration tank.

Further the particle size and morphology obtained by the present invention process is similar to that of ball milling process as shown in Table 3. However the current process is much more efficient and economical compared to the ball mill process. The particle size analysis is measured by Liquid particle counter.

TABLE 3

Comparison of particle size between present invention formulation of brinzolamide ophthalmic suspension 1.0% and Reference listed drug (AZOPT(R)).

| Particle size | RLD Lot No. 203411F | Present Invention Lot No. PR3F054-10 |
|---|---|---|
| % ≤10μ Particles | 94.0% | 99.0% |
| % ≤25μ Particles | 100.0% | 100.0% |
| % ≤50μ Particles | 100.0% | 100.0% |
| % ≤100μ Particles | 100.0% | 100.0% |

For development studies, particle size evaluation has been also performed using Morphology G3 instrument from Malvern at Aimil Labs in Vadodara as shown in Table 4.

TABLE 4

Comparison of particle size between present invention formulation of brinzolamide ophthalmic suspension 1.0% and Reference listed drug (AZOPT(R))

| Particle size | RLD 203411F | Present Invention PR3F054-10 |
|---|---|---|
| D(0.9) | 1.89μ | 3.02μ |
| D(0.5) | 1.21μ | 2.01μ |
| D(0.1) | 0.75μ | 1.38μ |

From the particle size analysis as depicted above in Table 4, it is inferred that present invention formulation of brinzolamide ophthalmic suspension 1.0% is comparable with Reference listed drug i.e. AZOPT®, manufactured by Alcon Pharmaceuticals.

UTILITY OF THE PRESENT INVENTION

The present inventors provides a simpler, cost effective and efficient process for manufacturing sterile, ophthalmic pharmaceutical suspension comprising CAI without the use of use of any special equipment such as ball mill, milling bottle and/or, jet mill. The prepared suspension is useful in treatment of elevated intraocular pressure in patients with ocular hypertension or, open angle glaucoma.

The invention claimed is:

1. An improved process of manufacturing a sterile, ophthalmic pharmaceutical suspension comprising sterile brinzolamide having a particle size of less than or equal to 25 μ, at least one surfactant, wherein each surfactant is independently selected from 4-(1,1,3,3-Tetramethylbutyl)phenol polymer with formaldehyde and oxirane, (a-[4-(1,1,3,3-tetramethylbutyl)phenyl]-co-hydroxypolyoxy-1,2-ethanediyl), polysorbates, polyoxyl 35 castor oil, polyoxyl 40 hydrogenated castor oil, polyoxyl 40 stearates, sorbitan monolaureates, poloxamer, and combinations thereof, wherein the process consists essentially of the steps of:
   i. subjecting a suspension of the sterile brinzolamide in an aqueous solution of surfactant to homogenization to form a mixture, wherein the process:
      a) excludes sterilization of active ingredient prior to homogenization through autoclaving technique,
      b) does not involve the use of any special equipment's such as ball mill, milling bottle and/or jet mill to achieve desired particle size; and,
   ii. combining the mixture formed in step i with inactive ingredients, wherein the inactive ingredients comprise:
      a) at least one polymer, wherein each polymer is independently selected from poly(acrylic acid), povidone, hydroxypropyl methyl cellulose, hydroxypropyl cellulose, hydroxyethyl cellulose, and combinations thereof,
      b) at least one or two tonicity agent(s), wherein each tonicity agent is independently selected from mannitol, dextrose, glycerin, potassium chloride, sodium chloride, and combinations thereof,
      c) optionally at least one chelating agent, and
      d) optionally a pharmaceutically acceptable preservative, wherein the ophthalmic pharmaceutical suspension, upon storage for three months, comprises less than 0.4 w/v % of (S)-4-(ethylamino)-3,4-dihydro-2-(3-methoxypropyl)-2H-thieno[3,2-e]-1,2-thiazine-6-sulfonamide 1,1-dioxide and the ophthalmic pharmaceutical suspension is stable when stored for 3 months at 40° C. at no more than 25% relative humidity.

2. The process as claimed in claim 1, wherein the manufacturing process reduces generation of (S)-4-(ethylamino)-3,4-dihydro-2-(3-methoxypropyl)-2H-thieno[3,2-e]-1,2-thiazine-6-sulfonamide 1,1-dioxide.

3. The process as claimed in claim 1, wherein the at least one surfactant is 4-(1,1,3,3-Tetramethylbutyl)phenol polymer with formaldehyde and oxirane.

4. The process as claimed in claim 1, wherein the at least one polymer is poly(acrylic acid).

5. The process as claimed in claim 1, wherein the preservative is selected from benzethonium chloride, phenyl ethanol, phenyl propanol, phenyl mercuric acetate, phenyl mercuric nitrate, phenyl mercuric borate, chlorhexidine acetate or gluconate, cetrimide, chlorocresol, sodium methyl paraben, sodiumpropyl paraben, thimerosal, benzalkonium chloride and combinations thereof.

6. The process as claimed in claim 1, wherein the at least one or two tonicity agent are each independently selected from mannitol, sodium chloride, and combinations thereof.

7. The process as claimed in claim 1, wherein each chelating agent is independently selected from edetate disodium, edetate trisodium, edetate tetrasodium, diethyleneamine pentaacetate, and combinations thereof.

8. The process as claimed in claim 1, wherein homogenization is carried out by using high pressure homogenization at pressure 1000±200 bar for uniform dispersion.

9. A sterile, ophthalmic pharmaceutical suspension as prepared by the process as claimed in claim 1.

10. The process as claimed in claim 1, wherein the ophthalmic pharmaceutical suspension is packaged in a multi dose container.

11. The process as claimed in claim 1, wherein the ophthalmic pharmaceutical suspension is packaged in a unit dose container.

12. A method of treating elevated intraocular pressure in a patient suffering from ocular hypertension or primary open angle glaucoma, the method comprising applying at least once a day to an eye of the patient in need thereof the ophthalmic pharmaceutical suspension of claim 9.

13. The method of claim 12, wherein the applying is done twice a day.

14. The method of claim 12, wherein the applying is done once a day.

15. A process of manufacturing a sterile, ophthalmic pharmaceutical suspension comprising brinzolamide, wherein the process consists essentially of the steps of:
   a) preparing a solution comprising one or more polymers, one or more chelating agents, one or more tonicity agents and optionally a pharmaceutically acceptable preservative, wherein at least one of the polymers is poly(acrylic acid), wherein at least one of the chelating agents is edetate disodium, and wherein at least one of the tonicity agents is mannitol, sodium chloride, or a combination thereof;
b) adjusting the pH of the solution of step a) between 7.5±0.3 by adding sodium hydroxide/hydrochloric acid, in increments, if required;
c) sterilizing the bulk of step a) by in-situ sterilization;
d) preparing a surfactant solution in another pressure vessel;
e) filtering a surfactant solution of step d) through 0.2 µfilter;
f) preparing a slurry by adding aseptically sterile brinzolamide having a particle size of less than or equal to 25 µ to the above surfactant solution of step e) wherein the process excludes sterilization of active ingredient through autoclaving prior to adding to step e;
g) homogenizing the above slurry using high pressure homogenizer at pressure 1000±200 bar to achieve uniform dispersion;
h) transferring this homogenized slurry into sterile bulk in filtration tank of step c);

wherein the ophthalmic pharmaceutical suspension, upon storage for three months, comprises less than 0.4 w/v% of (S)-4-(ethylamino)-3,4-dihydro-2-(3-methoxypropyl)-2H-thieno[3,2-e]-1,2-thiazine-6-sulfonamide 1,1-dioxide and the ophthalmic pharmaceutical suspension is stable when stored for 3 months at 40° C. at no more than 25% relative humidity.

* * * * *